United States Patent [19]

Boersen et al.

[11] Patent Number: 5,294,199

[45] Date of Patent: Mar. 15, 1994

[54] SYSTEM AND METHOD FOR THERMALLY STRESS SCREENING PRODUCTS

[75] Inventors: Harry D. Boersen; John M. Eldred, both of Holland; Robert K. Hayes, Fruitport; Vince J. Jasinski, Grand Rapids; Kim A. Pattee; Clinton A. Peterson, both of Holland; David L. Walcott, Zeeland, all of Mich.

[73] Assignee: Venturedyne, Ltd., Milwaukee, Wis.

[21] Appl. No.: 968,547

[22] Filed: Oct. 29, 1992

[51] Int. Cl.$^5$ .............................................. G01N 3/60
[52] U.S. Cl. ........................................ 374/57; 374/5; 165/61
[58] Field of Search ............... 374/4, 5, 45, 50, 57; 73/865.6; 324/158 F; 165/18, 48.1, 61; 34/73, 77, 78

[56] References Cited

U.S. PATENT DOCUMENTS

| | | | |
|---|---|---|---|
| 3,656,058 | 4/1972 | Leathers | 324/158 F |
| 4,476,867 | 10/1984 | Parks | 165/61 X |
| 4,483,629 | 11/1984 | Schwarz et al. | 374/57 |
| 4,602,503 | 7/1986 | Hile et al. | 73/865.6 |
| 4,627,287 | 12/1986 | Suga | 73/865.6 |
| 4,628,616 | 12/1986 | Shirai et al. | 34/78 |
| 4,683,424 | 7/1987 | Cutright et al. | 324/158 F |
| 4,695,707 | 9/1987 | Young | 324/158 F X |
| 4,733,973 | 3/1988 | Machak et al. | 374/5 |
| 5,004,973 | 4/1991 | Tarachi et al. | 324/158 F X |
| 5,039,228 | 8/1991 | Chalmers | 374/57 |

FOREIGN PATENT DOCUMENTS

| | | | |
|---|---|---|---|
| 60-144638 | 7/1985 | Japan | 374/57 |
| 4-242144 | 8/1992 | Japan | 374/57 |
| 4-254736 | 9/1992 | Japan | 374/57 |

Primary Examiner—William A. Cuchlinski, Jr.
Assistant Examiner—G. Bradley Bennett
Attorney, Agent, or Firm—Jansson & Shupe, Ltd.

[57] ABSTRACT

The invention is an improvement in a thermal stress screening system of the type using a single type of liquid for alternately transferring heat to and from the product. In the improvement, the product is confined in a single chamber during alternate heat transfer. That is, the system provides "one chamber" thermal stress screening. The system includes a plurality of tanks, one each for hot and cold liquid, and a heat exchanger associated with each tank so that the liquid in a tank is maintained at the proper temperature for stress screening. An improved method for thermally stress screening products, e.g., printed circuit boards, includes the steps of placing the product in a chamber, flowing cold liquid into the chamber, draining the cold liquid from the chamber and flowing hot liquid into the same chamber.

22 Claims, 9 Drawing Sheets

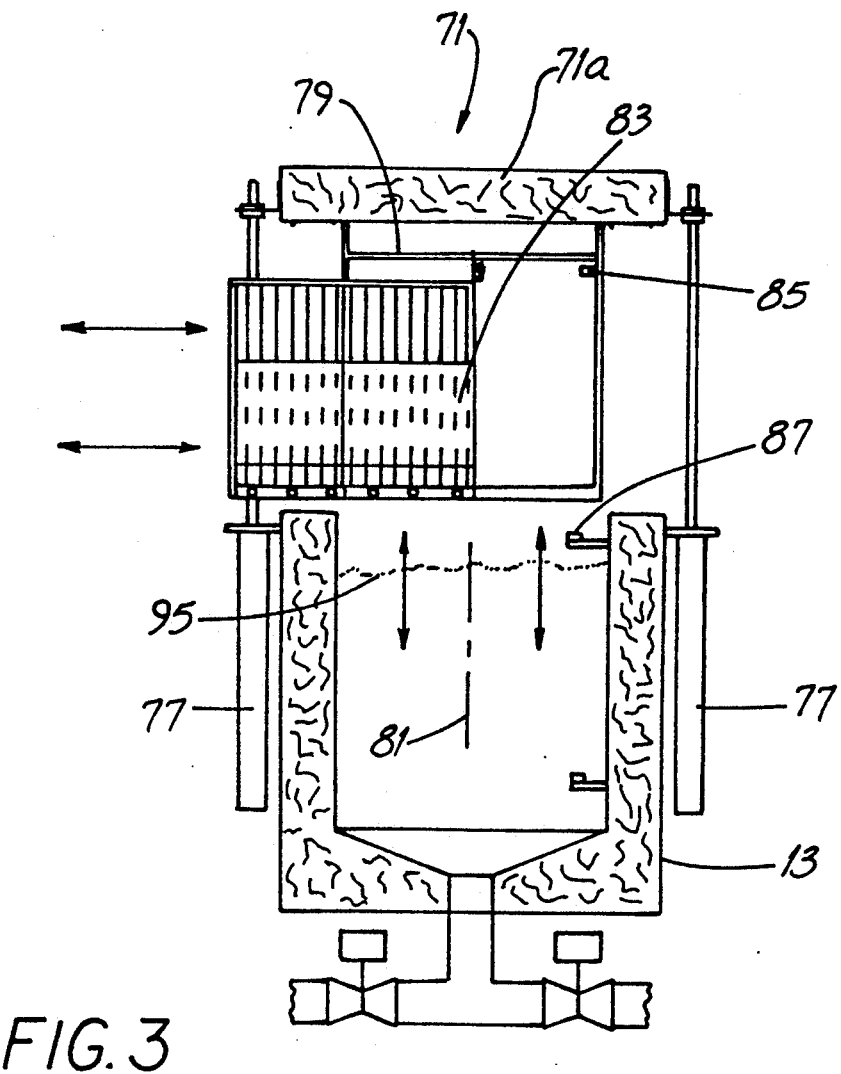

SYSTEM AND METHOD FOR THERMALLY STRESS SCREENING PRODUCTS

FIELD OF THE INVENTION

This invention relates generally to product testing and, more particularly, to product testing by what is known as "stress screening."

BACKGROUND OF THE INVENTION

Certain types of products, including printed circuit boards for electrical apparatus, may be used in operating environments which subject such products to rigors well beyond those experienced by, e.g., a printed circuit board in a household television set. Military equipment, aircraft radar devices for example, are often required to be constructed of components which have been rigorously tested so that they are durable in such operating environments. One type of unusual operating environment involves temperature extremes. As an example of such an environment, a high performance military aircraft may fly from ground level (perhaps in the hot desert) to a very high, cold altitude in a very short time.

And manufacturers of such products and their customers have long been aware that product "stress screening" is an effective way to "prove" a product configuration and cull out products which may fail prematurely. Stress screening may include rapid sequential exposure to extremes of, for example, vibration, humidity or temperature. The invention relates to thermal stress screening during which products are repetitively exposed to temperature extremes, e.g., temperatures well below the freezing point and well above the boiling point of water.

It is common to thermally stress screen printed circuit boards by, for example, rapidly changing their temperature from about $-20°$ C. or even about $-40°$ C. (about equal to $-6°$ F. and $-40°$ F., respectively) up to about $125°$ C. which is about equal to $260°$ F. It is easy to understand why testing systems imposing such rapid temperature extremes are sometimes referred to as "thermo-shock" systems.

A known way to thermally stress screen circuit boards is to place such boards within a thermal stress chamber (often called an environmental test chamber) and alternately force very hot air and very cold air through the chamber for the time required to bring the board temperature to the required high or low level. Of course, the air used for a particular hot or cold cycle is simply drawn from the room ambient and heated or chilled, as needed. Examples of environmental test devices are shown in U.S. Pat. Nos. 3,656,058 (Leathers); 4,683,4224 (Cutright et al.) and 4,695,707 (Young). A leading manufacturer of environmental test chambers (as well as other stress screening products) is Thermotron Industries, Inc. of Holland, Mich.

While environmental test chambers using heated or chilled forced air have been highly satisfactory, using air as the thermal transfer medium requires a significant amount of time to repetitively change the temperature of the circuit board from one extreme of temperature to the other. Total process time on the order of a few hours for a particular group of boards being screened is not unusual. For a chamber cavity capable of holding a given number of circuit boards, it is apparent that there is some maximum number of boards that can be screened per unit time. Therefore, the product "throughput" for that test chamber can be calculated.

Efforts to shorten the total process time for a given number of circuit boards have included using liquid as the thermal transfer medium and contacting printed circuit boards directly with such liquid. With this arrangement, overall process times can be reduced by a ratio of perhaps 5:1 or even 10:1. Such efforts in this field have included using two liquid tanks (one each for hot and cold liquid) and a different type of liquid in each tank. Circuit boards are moved to one tank and then to the other and the particular type of liquid in a tank was selected in view of whether it will be used to heat or chill the boards.

Even with two tanks, the use of two different types of liquids ultimately results in "cross-contamination" and the liquids must be discarded or at least the contaminating liquid removed therefrom. Cross-contamination occurs since some liquid clings to the boards as they are being transferred to the other tank. More recently, the problem of cross-contamination has been resolved by using a single type of liquid in both tanks. But the problem of transferring a relatively large number of printed circuit boards (which may have appreciable total weight) between tanks still remains. And since printed circuit boards are usually electrically energized during thermal screening, the problem of connecting, disconnecting and re-connecting such boards (or using a rather long "pigtail" connection) also remains.

An improved thermal stress screening system and method which avoid transferring products between liquid tanks, which dramatically shortens overall process time and which conserves the thermal transfer liquid would be an important advance in the art.

OBJECTS OF THE INVENTION

It is an object of the invention to provide an improved system and method for thermally stress screening products which overcomes some of the problems and shortcoming of the prior art.

Another object of the invention is to provide an improved system and method for thermally stress screening products which avoid transferring products to be screened between tanks or chambers.

Another object of the invention is to provide an improved system and method for thermally stress screening products which substantially avoid liquid contamination.

Still another object of the invention is to provide an improved system and method for thermally stress screening products which use a single type of liquid.

Another object of the invention is to provide an improved system and method for thermally stress screening products which dramatically reduces overall process time.

Yet another object of the invention is to provide an improved system and method for thermally stress screening products which help conserve the thermal transfer liquid.

Another object of the invention is to provide an improved system and method for thermally stress screening products which avoids repetitive electrical product disconnection and re-connection. How these and other objects are accomplished will become more apparent from the following descriptions.

SUMMARY OF THE INVENTION

The invention is an improvement in a thermal stress screening system using a single type of liquid for alternately transferring heat to and from the product. In the improvement, the product is confined in a single chamber during alternate heat transfer. That is, the invention permits "one chamber" thermal stress screening of products, e.g., generally planar printed circuit boards, using a liquid.

The chamber may be configured in any of several ways to permit placement of boards into it. In one preferred arrangement, the chamber includes a top access door powered for raising and lowering the door with respect to the chamber. There is also a rack-like, door-supported carrier for receiving and holding the circuit boards and for placing them into the chamber. Powered movement of the door and carrier is particularly desirable when loading a carrier "top down" into the chamber. Together, the boards and carrier are relatively heavy and somewhat difficult to handle manually. And, as described below, the boards are attached by multi-prong sockets and mating plugs to test instruments outside the chamber. Such sockets and plugs are "high insertion force" devices. Therefore, powered connection of them is desirable, especially when pushing downward from the top of the chamber.

In another chamber configuration, the chamber includes a side access door. Since it is easier for a system operator to push sideways rather than "top down," powered operation may not be required. In this configuration, the door has an inner seal, an outer lip and a liquid recovery drain between the outer lip and the inner seal. In the event the thermal transfer liquid (which is quite expensive) leaks past the door seal, it flows to the drain and is recovered rather than flowing onto the room floor.

When thermally stress screening electrical products which are energized during screening, it is better if the multi-prong plugs and sockets are kept out of the liquid. In a typical arrangement having a movable carrier, there is a first stationary connector mounted in the chamber cavity and a second connector wired to the first connector and mounted to move with the carrier. Preferably, the connectors are above the top surface of the liquid.

Since such boards are somewhat fragile and since it is preferred to rapidly transfer liquid into and out of the chamber, there could be some possibility of board damage due to the "flow forces" of the liquid which, preferably, is more dense than water and has a mass per unit volume well in excess of that of water. Accordingly, in a highly preferred arrangement, the liquid is introduced into and removed from the chamber in a coplanar direction, i.e., toward and away from the edges of the boards rather than toward the board broad surfaces.

Liquid is introduced into the main chamber cavity through a pipe-like liquid flow port. Liquid "gushing" into such main cavity in columnar flow, even in a coplanar direction, could damage the circuit boards. In a highly preferred embodiment, a diffuser is interposed between the liquid flow port and the cavity. The diffuser "breaks up" the flow column so that liquid flows into the cavity along and across substantially the entirety of the cavity bottom area.

The chamber is preferably sealed and, of course, as liquid enters and leaves the chamber, gas needs to be displaced from or permitted to re-enter the chamber. That is, chamber pressure should be "normalized" essentially at room ambient pressure to prevent overpressuring the chamber and to prevent drawing a partial vacuum therein. Therefore, the chamber includes at least one port substantially normalizing chamber pressure and liquid level during liquid transfer.

During thermal stress screening, cold liquid and hot liquid are alternately transferred into and out of the chamber to substantially immerse the circuit boards. The system includes a hot tank and a cold tank containing the liquid at widely disparate temperatures for alternate transfer to the chamber.

Each tank has a separate heat exchanger in flow communication with it. During, e.g., a cold cycle portion of the process, the liquid is introduced into the chamber at a depressed temperature. The cold tank and that heat exchanger in flow communication with such tank comprise a cold "conditioning" loop. Such loop conditions the liquid removed from the chamber (which has been warmed somewhat by contact with the chamber and the boards) by cooling it and retaining it in the cold tank substantially at the depressed temperature. In that way, such liquid is at the right temperature for immediate redelivery "on demand" to the chamber.

During a hot cycle portion of the process, some liquid is vaporized in the chamber. To help avoid loss of vaporized liquid when the chamber door is opened (and consequent liquid replenishment), it is preferred that such vaporized liquid be recovered. To that end, a preferred cold conditioning loop includes a vapor condenser. Such condenser may comprise the cold walls of the piping system or of the chamber whereby vaporized liquid may be recovered.

Or the vapor condensor may be a cryogenic heat exchanger or a mechanical refrigeration-type heat exchanger. The preferred condenser takes advantage of the extreme cold prevailing in the cold tank liquid and includes a multi-flowpath device, e.g., plural fin-like spaced parallel plates, in such tank.

The overall process time required to stress screen a group of circuit boards depends in significant part upon the time required to transfer liquid into and out of the chamber. If the transfer time can be shortened, so can the overall process time. Thus, the same system can be more efficiently and economically used to screen a greater number of boards per unit time.

The time required to transfer liquid into the chamber can be reduced by using a larger delivery pump. With the liquid piping network and the tanks below the chamber and with a drain pipe extending from the chamber to a particular tank (hot or cold), gravity is a reliable way to transfer liquid out of the chamber. However, this may well be slower than actively pumping the liquid out of the chamber. In the preferred embodiment, such transfer is expedited by an outflow pump embodied as a venturi eductor connected to the drain pipe for urging liquid from the chamber toward the tank. Of course, pressurizing the chamber offers much the same result.

While unlikely, there is a possibility that the tanks, the piping system and/or the chamber may develop leaks. The preferred liquid (details of which are described below) is very expensive and, if possible, should be prevented from being wasted. The preferred system includes a plurality of tanks for containing the liquid, a piping network in flow communication with the tanks and the chamber and a drip receptacle below the tanks and the network. The receptacle has a liquid level switch (e.g., a float switch) disabling the system when the liquid in the receptacle reaches a predetermined level.

Since both the hot and cold tanks contain the same type of liquid (but at widely differing temperatures), the preferred system also has an interflow line extending between the tanks. Such line functions as an overflow line (much like the overflow port in a wash basin) and prevents the volume of liquid in a tank from exceeding a predetermined volume.

Aspects of the invention also include an improved method for thermal stress screening products by using a single type of liquid for alternately transferring heat to and from the product. Such method includes the steps of placing the product in a chamber, flowing cold liquid into the chamber, draining the cold liquid from the chamber and flowing hot liquid into the same chamber. In the inventive method, the cold liquid flowing step includes flowing cold liquid into the chamber at a depressed temperature and the cold liquid draining step is followed by the step of conditioning (by removing heat from) the drained cold liquid to a temperature substantially equal to the depressed temperature.

The preferred liquid is more dense than water. Therefore, any water which becomes entrained in the liquid eventually migrates to the liquid top surface. If present while electrically-energized circuit boards are in the chamber, water could be very damaging. Therefore, in the preferred method, the product placing step is followed by the step of dehumidifying the chamber. Dehumidifying may be by purging the chamber with a substantially dry gas, e.g., air or nitrogen, by mechanical refrigeration with dehumidification coils or by using a dessicant dryer. Such dehumidifying prevents water from contaminating the liquid.

As noted above, the chamber will contain vaporized liquid following a hot liquid flowing step. Therefore, at least one of the hot liquid flowing steps is preferably followed by the step of recovering vaporized liquid from the heated chamber. Such recovery includes flowing vaporized liquid through a condenser.

When vaporized liquid is thus recovered, the remaining substantially vapor-free air stream is chilled to a temperature well below room ambient temperature. For reasons that will be described, recovering vaporized liquid preferably includes delivering chilled air to the chamber. Such chilled air reduces the temperature of the chamber walls in anticipation of opening the chamber door and permitting entry of ambient air.

However, reducing the temperature of such walls too severely, i.e., below the dew point of the ambient air in the room in which the chamber is located, could result in moisture condensation on the chamber walls. And, as noted above, the presence of moisture in the system is undesirable. Therefore, it is preferred that de-vapored chilled air is delivered to the chamber until the temperature of the chamber wall is reduced to within a few degrees above the ambient temperature in that room. In that way, moisture condensation is substantially avoided even though the relative humidity in the room may be near 100%.

The preferred method may be carried out in a two-chamber system as well as in a one-chamber system. In a two-chamber system, the improved method for thermally stress screening products includes the steps of placing a first group of products into a first chamber, flowing cold liquid into the chamber and then draining the cold liquid from the chamber. Further steps include flowing hot liquid into the same chamber and in any order with respect to the placing, flowing and draining steps, the step of placing a second group of products into a second chamber. Therefollows the steps of flowing cold liquid into the second chamber, draining the cold liquid from the second chamber and flowing hot liquid into the second chamber.

Described in different terms with respect to a two-chamber arrangement, the products in one chamber are screened by repetitively, alternately using the cold stress and hot stress portions of the process to screen the products in that chamber. While this is occurring, the second chamber may be emptied of screened products and re-loaded with products to be screened. Then the process is carried out with respect to the products in the second chamber while the first chamber is being emptied and re-loaded. Those portions of the overall process which are most time-consuming are dehumidifying and vapor recovery. Using a single network with two chambers helps reduce the time during which no product is being screened.

It is possible to carry out the process in a two-chamber arrangement by using a cold cycle portion on products in one chamber while using a hot cycle portion on products in the other chamber and then alternating portion application. While such an arrangement is entirely operative, the piping system would be more complex and substantially more heat exchange capacity would be needed.

Further details of the invention are set forth in the following detailed description and the drawing.

BRIEF DESCRIPTION OF THE DRAWING

FIG. 2 is a graphic table showing the symbols for various valve positions and for a system filter component.

FIG. 3 is a representative cross-section side elevation view of one embodiment of a system chamber, i.e., a powered top loaded chamber. Parts are broken away.

DETAILED DESCRIPTION OF PREFERRED EMBODIMENTS

Figure 1:
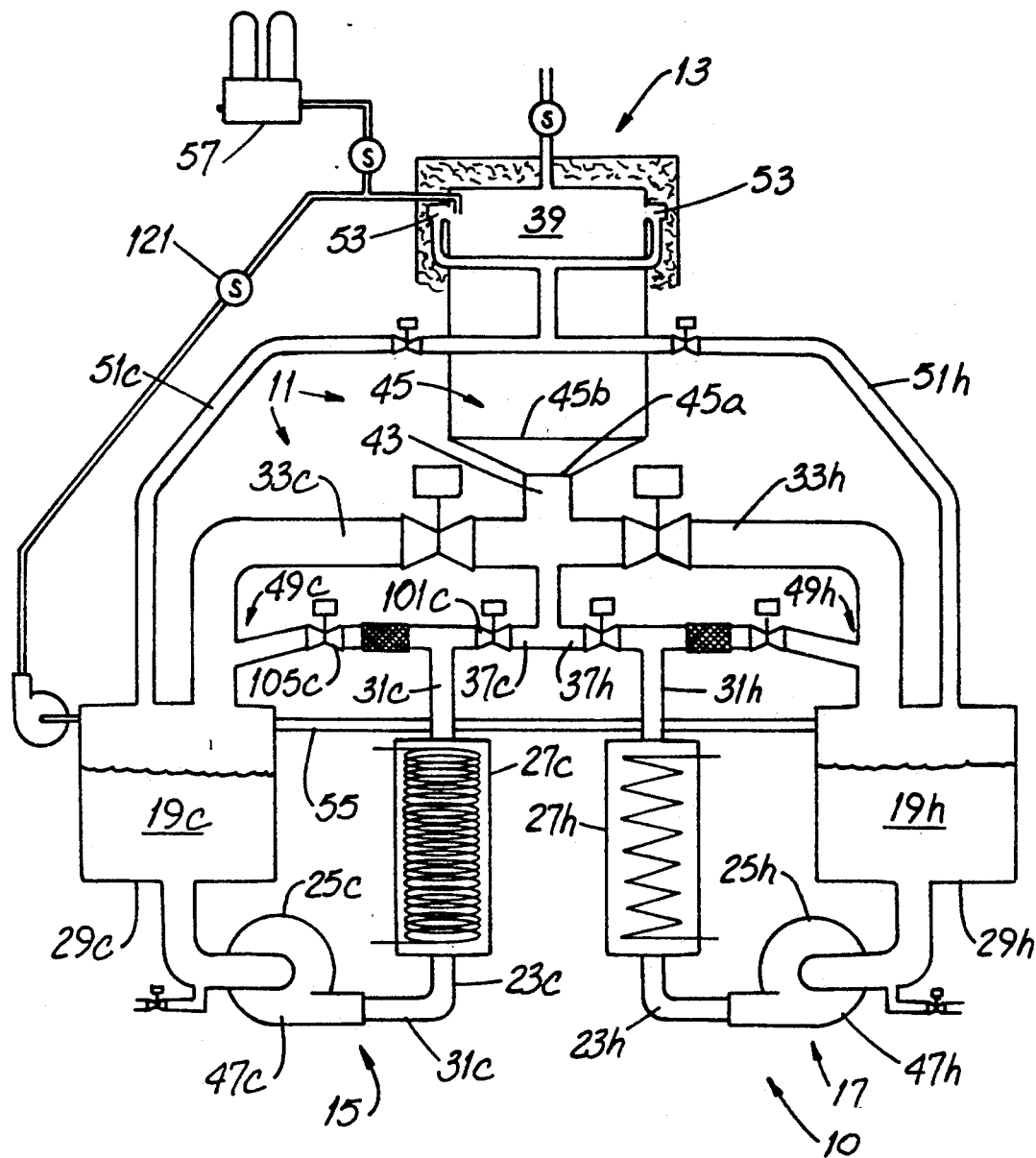
FIG. 1 is a representative diagram of the inventive system (including the chamber, piping and valves) without regard to the open or closed position of the system valves. Parts are shown in cross-section and parts are broken away.

The improved thermal stress screening system 10 is generally depicted in FIG. 1. The arrangement of the piping network 11 (including connection of pipes to the chamber 13 and also including ancillary equipment) will be described first and will be followed by a description of various chamber configurations. The various portions or stages of operation of the system 10 will then be described.

The Piping Network

The system 10 includes a piping network 11 having a cold unit 15 and a hot unit 17. The fundamental purpose of each unit 15, 17 is to condition and have ready a quantity of cold liquid 19c or hot liquid 19h for delivery to and later recovery from the chamber 13 in which products to be tested are placed. While the network 11 has a number of valves including solenoid valves, the position of such valves, i.e., open or closed as indicated in the symbol system diagram of FIG. 2, is random in the view of FIG. 1. And as will become apparent, the units 15, 17 are generally "mirror images" of one another. Therefore, the units 15, 17 are generally described using the cold unit 15 as an example. A particular component of the cold unit 15 is identified by a "c" suffix while the corresponding component of the hot unit 17 is identified by an "h" suffix.

The cold unit 15 includes a cold conditioning loop 23c comprised of a liquid pump 25c and the unit heat exchanger 27c which may be cooled by a mechanical or cryogenic heat removal device. Such loop 23c also includes the cold liquid tank 29c and the connecting pipes 31c. The conditioning loop 23c receives liquid 19c from the chamber 13 via a unit return line 33c and circulates such liquid 19c within the loop 23c while "conditioning" it. For liquid 19c flowing from the chamber 13 to the conditioning loop 23c (and which carries heat removed from the product 35 and the chamber 13 itself), liquid conditioning includes removing heat by the heat exchanger 27c and returning the liquid 19c to the cold tank 29c.

The temperature of such liquid 19c is thereby reduced to what is referred to as a "depressed temperature." As used herein, the depressed temperature is that at which the cold liquid 19c is ready for transfer into the chamber 13. The depressed temperature is preferably below about 0° C. (about 32° F.) and most preferably about −20° C. to about −40° C., depending upon the requirements of the screening process. Reference is also made in this specification to liquid 19h at an "elevated temperature." As used herein, the elevated temperature is that at which the hot liquid 19h is ready for transfer into the chamber 13. The elevated temperature is preferably above about 20° C. (about 65° F.) and most preferably above 100° C. (about 212° F.), i.e., at about 125° C. (about 260° F.).

The cold unit 15 also includes a feed line 37c through which cold liquid 19c is transferred to the chamber cavity 39. Liquid 19c transferred from the cavity 39 flows through the return line 33c. The feed lines 37c, 37h and the return lines 33c, 33h are joined to one another and to a common flow port 43 connected to the bottom of the chamber 13. For reasons later described, a diffuser 45 is interposed between the liquid flow port and the cavity. The diffuser 45 "breaks up" the column of liquid flowing up through the port 43 so that liquid flows into the cavity 39 along substantially the entirety of the cavity bottom area rather than "geyser-like." The diffuser 45 may comprise a screen 45a or in a variant embodiment, the chamber 13 may include both a screen 45a and a perforated diffuser plate 45b.

In pumping direction, the pump 47c draws liquid 19c from the tank 29c and delivers it around the loop 23c or to the feed line 37c and thence to the chamber 13, depending upon valve position. It is therefore apparent that to a large degree, liquid 19c can be "forced" into the chamber by the pump 47c.

On the other hand, the illustrated physical layout (with the chamber 13 mounted above the piping network 11) is suitable for gravity transfer of the liquid 19 from the chamber 13 to a tank 29. In the preferred embodiment, such transfer is expedited by an outflow pump 49 preferably embodied as a venturi eductor connected to the return line 33c for urging liquid 19 from the chamber 13 toward a tank 29. Of course, pressurizing the chamber 13 or placing an additional pump (not shown) in the return line 33 offers much the same result.

As liquid 19 is transferred to or from the chamber 13, air (or other purging gas as described below) must, respectively, be displaced out of the chamber 13 or must displace the removed liquid 19 in the chamber 13. Therefore, the system 10 also has a separate normalizing or equalizing line 51c, 51h extending between the chamber 13 and each tank 29c, 29h for maintaining a liquid level and maintaining the system 10 at substantially ambient pressure. For example, as liquid 19c flows from the chamber 13 along the return line 33c to the cold tank 29c, air in the cold tank 29c is displaced, flows up the line 51c and through the ports 53 and prevents the pressure in the chamber 13 from dropping below ambient. There is also an interflow line 55 extending between the tanks 29c, 29h to prevent the volume of liquid in a tank from exceeding a predetermined volume. The lines extending between the ports 53 and the lines 51 are outside of the chamber cavity 39.

Since the preferred liquid 19 is heavier than water, any water entering the system 10 may find its way to the top of the liquid level in the chamber 13 and damage circuit boards 35a as described above. Therefore, the system 10 also includes a dehumidifier 57 which, by valving, can be connected to the chamber 13 as needed. Dehumidifying may be by purging the chamber 13 with a substantially dry gas, e.g., air or nitrogen, or by using other dehumidification techniques as mentioned above.

Figure 10:
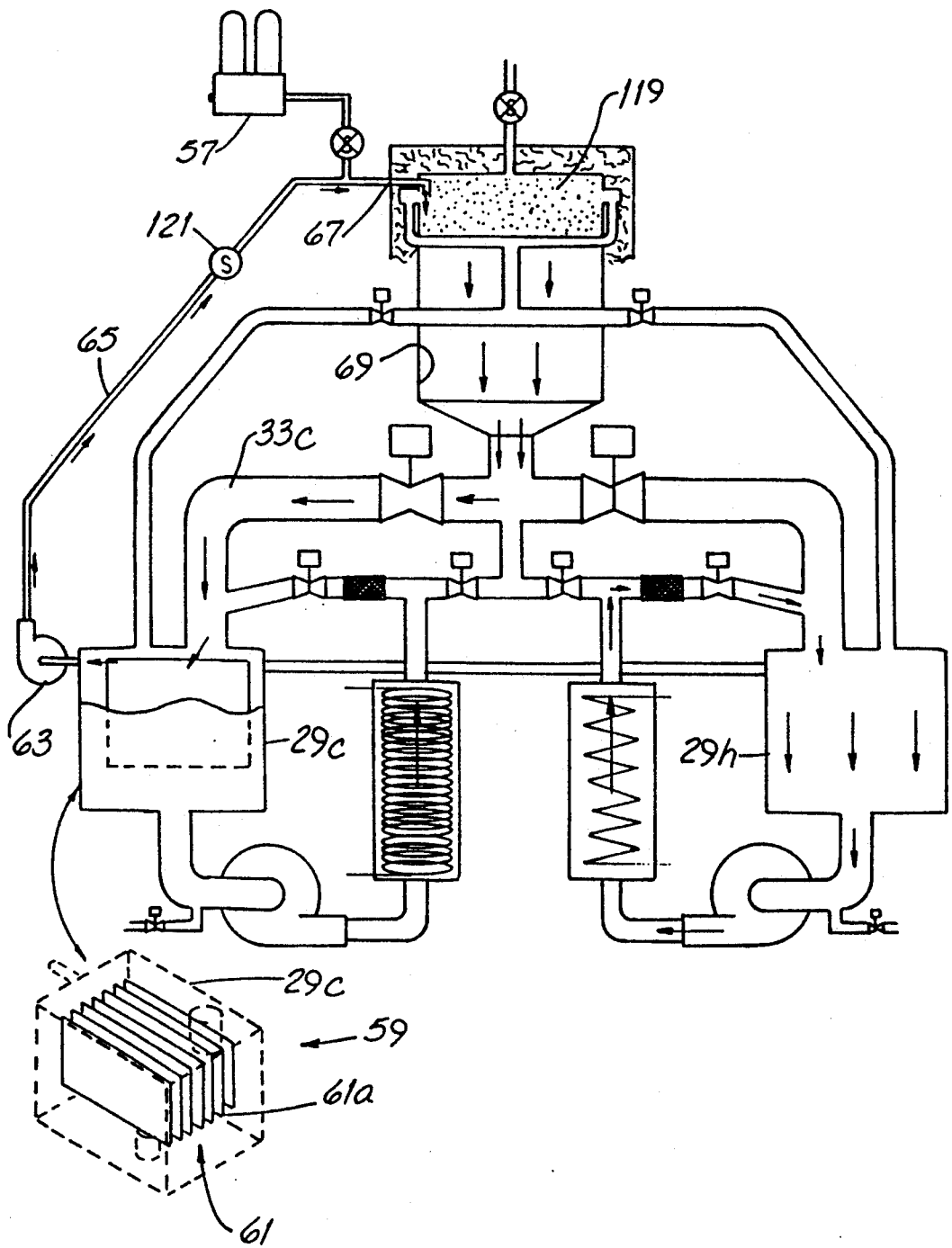
FIG. 10 is a representative diagram of the inventive system during a vapor recovery cycle of the thermal stress screening process. Parts are in cross-section and other parts are broken away.

During a hot cycle portion of the process (as described below), some liquid 19h is vaporized in the chamber 13. Referring also to FIG. 10, to help avoid continual liquid replenishment, it is preferred that such vaporized liquid be recovered. To that end, a preferred cold conditioning loop includes a vapor condenser 59. Such condenser 59 may comprise the cold walls of the piping network 11 or of the chamber cavity 39. Or the vapor condensor 59 may be a cryogenic heat exchanger or a mechanical refrigeration-type heat exchanger. The preferred condenser 5 takes advantage of the extreme cold prevailing in the cold tank 29c and its liquid 19c and includes a multi-flowpath device 61, e.g., plural fin-like spaced parallel plates 61a, in the cold tank 29c.

As a result of vaporized liquid being recovered, the remaining substantially vapor-free air is chilled to a temperature well below room ambient temperature. For reasons that will be described, the chilled air is drawn from the cold tank 29c by a blower 63 and delivered along the cold air line 65 through the port 67. Such chilled air reduces the temperature of the chamber walls 69. Wall temperature can be reduced to a few degrees above room ambient temperature to avoid water condensation on the walls 69 when the chamber door 71 is opened. There is no corresponding air line or air delivery system in the hot unit 17.

Figure 11:
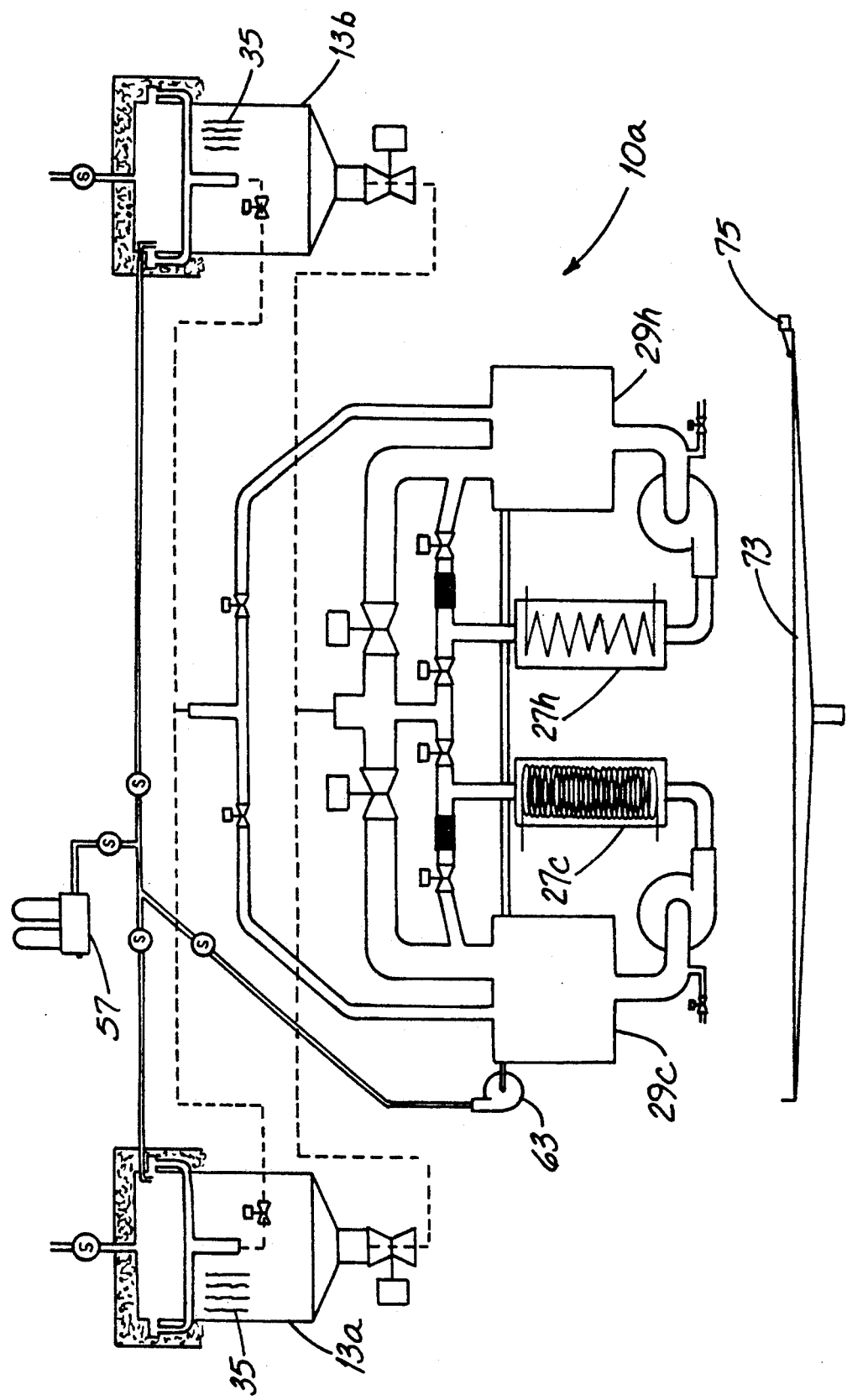
FIG. 11 is a representative diagram of another embodiment of the system involving the piping system of FIG. 1 with modifications and in conjunction with two chambers and a drip receptacle. Portions of the piping system are shown in dashed line, parts of the system are in cross-section and other parts are broken away.

In the unlikely event the tanks 29, the piping network 11 and/or the chamber 13 develop leaks, the preferred liquid 19 should be prevented from being wasted. As shown in FIG. 11, the preferred system 10 has a drip receptacle 73 below the tanks 29 and the network 11. The receptacle 73 preferably has a liquid level switch 75 (e.g., a float switch or other means) disabling the system 10 when the liquid 19 in the receptacle 73 reaches a predetermined level. Of course, the receptacle 73 may also be constructed to contain the entirety of the liquid 19 in the system 10 in which instance no switch 75 is required.

Those of ordinary skill will appreciate the advisability of well insulating the piping network 11 and the chamber 13, at least for energy conservation purposes.

Chamber Arrangements

Figure 4:
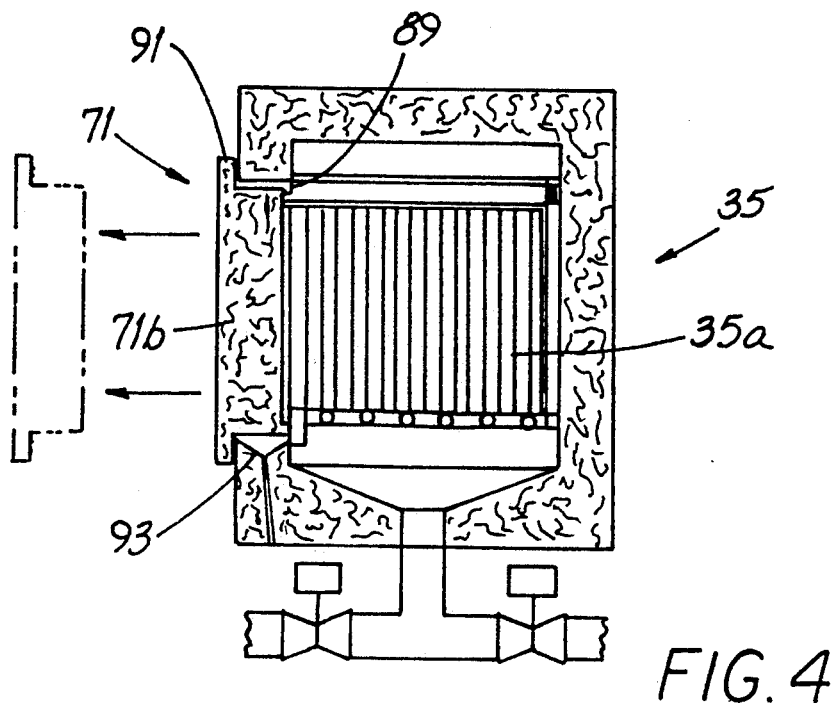
FIG. 4 is a representative cross-section side elevation view of another embodiment of a system chamber, i.e., a side loaded chamber. Parts are broken away.
Figure 5:
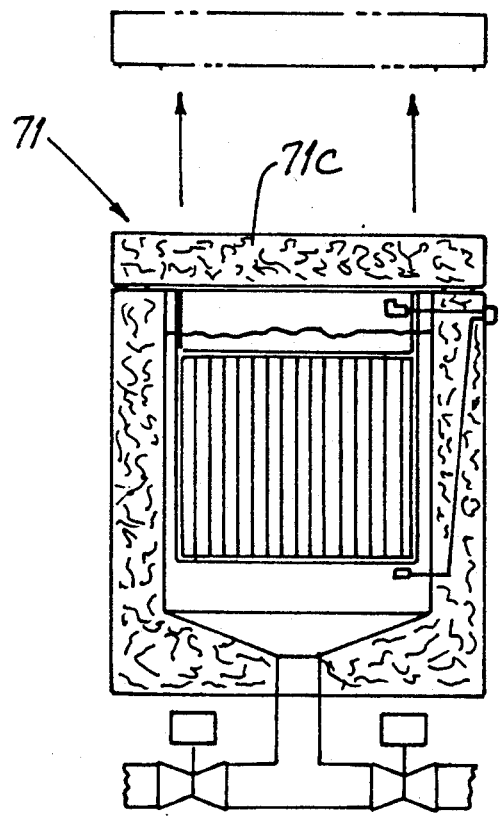
FIG. 5 is a representative cross-section side elevation view of yet another embodiment of a system chamber, i.e., a manually top loaded chamber. Parts are broken away.

Referring next to FIGS. 3, 4 and 5, the chamber 13 may be configured in any of several ways to permit placement of boards 35a into it. In one preferred arrangement shown in FIG. 3, the chamber includes a top access door 71a powered by cylinders 77 for raising and lowering the door 71a with respect to the chamber 13. There is also a rack-like, door-supported carrier 79 for receiving and holding the circuit boards 35a and for placing them into the chamber 13.

In a typical arrangement, all of the boards 35a in the carrier 79 are generally planar, are oriented parallel to the long axis 81 of the cavity 39 and are attached by edge connectors to one or more "mother boards 83." In turn, the mother board(s) 83 are connected by "pigtail" wiring harness to a plug 85 which moves with the carrier 79 and which attaches to a stationary socket 87 on the chamber wall 69 as the carrier 79 is urged into its final position.

Powered movement of the door 71a and carrier 79 is particularly desirable when loading a carrier 79 top down into the chamber 13. Together, the boards 35a and carrier 79 are relatively heavy and somewhat difficult to handle manually. And the aforementioned multi-prong sockets 87 and plugs 85 require high insertion and extraction forces to connect and disconnect them. Therefore, powered connection of them is desirable, especially when pushing downward from the top of the chamber 13.

In another chamber configuration shown in FIG. 4, the chamber 13 includes a side access door 71b. Since it is easier for a system operator to push sideways rather than top down, powered operation may not be required but is certainly an option. In this configuration, the door 71b has an inner seal 89, an outer lip 91 and a liquid recovery drain 93 between the outer lip 91 and the inner seal 89. In the event the thermal transfer liquid 19 leaks past the door seal 89, it flows to the drain 93 and is recovered before leaking out and spilling on the floor. In yet another chamber configuration shown in FIG. 5, the chamber 13 includes a manually-moved top door 71c.

Referring particularly to FIG. 3 when thermally stress screening electrical products which are energized during screening, it is better if the multi-prong plugs 85 and sockets 87 are kept out of the liquid 19. In a typical arrangement having a movable carrier 79, there is a first stationary connector 87 mounted on the chamber 13 and a second connector 85 wired to the first connector 87 and mounted to move with the carrier. Preferably, the connectors 85, 87 are above the top surface 95 of the liquid 19. If, however, the circuit arrangement requires multiple first and second connectors 85, 87 some of such connectors 85, 87 can be immersed during the process since the preferred liquid 19 is not electrically conductive.

Operation

Figure 6:
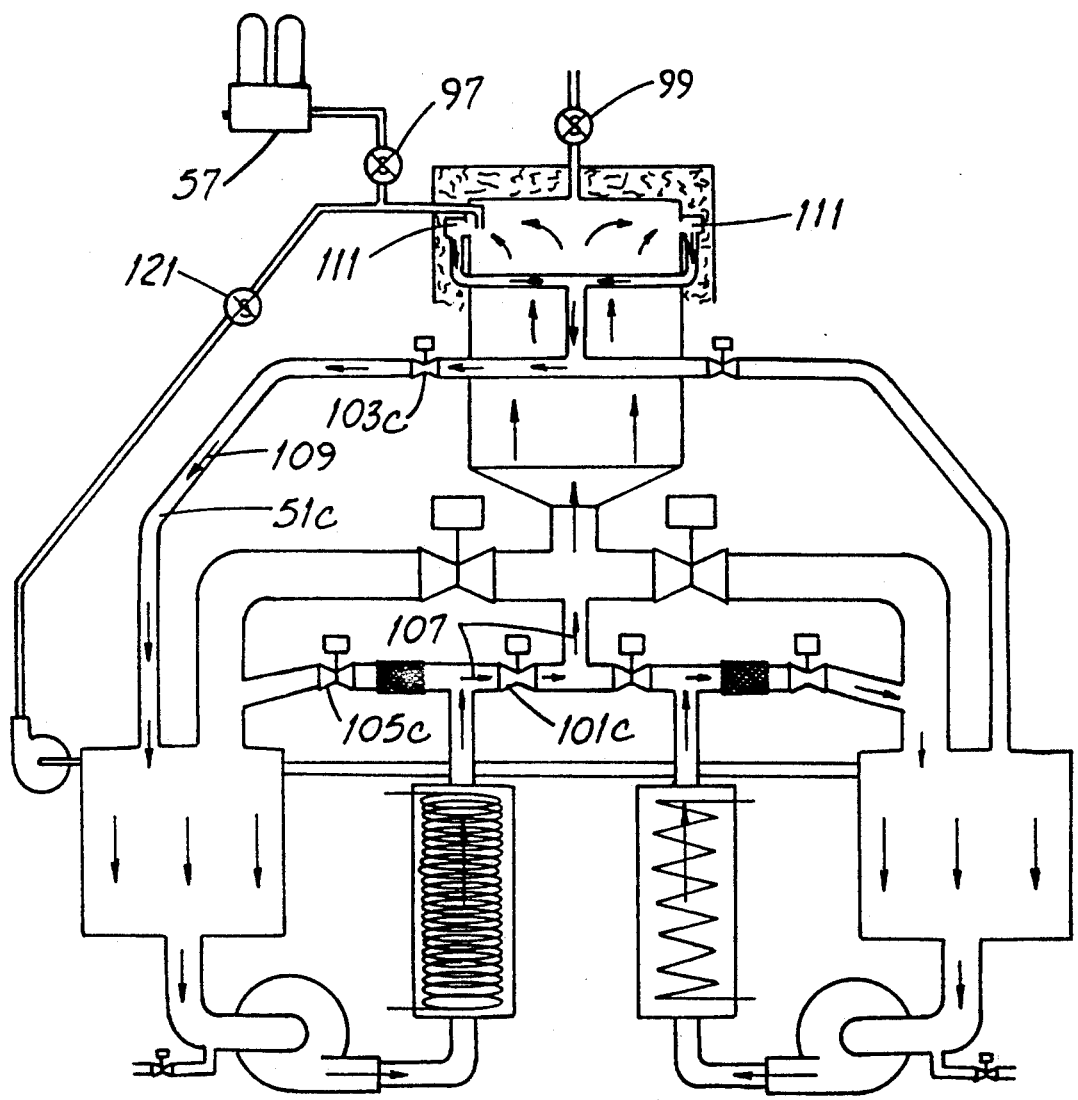
FIG. 6 is a representative diagram of the inventive system during a cold cycle portion of the thermal stress screening process. Parts are in cross-section and other parts are broken away.

Aspects of the invention also include an improved method for thermal stress screening products 35 by using a single type of liquid 19 for alternately transferring heat to and from the product 35. Referring now to FIG. 6 (and being mindful of the symbols of FIG. 2), a cold cycle portion of the thermal stress screening process will now be described.

It is assumed that the cavity 13 has been dehumidified, preferably by purging, by opening the purge valve 97 and the vent valve 99 and operating the dehumidifier 57 for the requisite time. It is also assumed that circuit boards 35a (or other products 35) have been placed in the chamber 13 and that the chamber 13 is sealed. The cold unit flow valve 101c and the cold unit normalizing valve 103c are then opened and the cold loop valve 105c is closed, thus causing cold liquid 19c to flow into the chamber 13. Liquid 19c (substantially at the depressed temperature) flows in the direction of the arrows 107 while dry air (or nitrogen, as the case may be) flows out of the chamber 13 along the normalizing line 51c and in the direction of the arrows 109 to fill the space in the tank 29c left by the transferred liquid 19c. Delivery of cold liquid 19c into the chamber 13 at the depressed temperature continues even though the chamber 13 fills until liquid overflows through the ports 111 and along the normalizing line 51c. Circulation of cold liquid 19c continues in this way until the temperature of the boards declines to the desired lower "set point" value.

Figure 7:
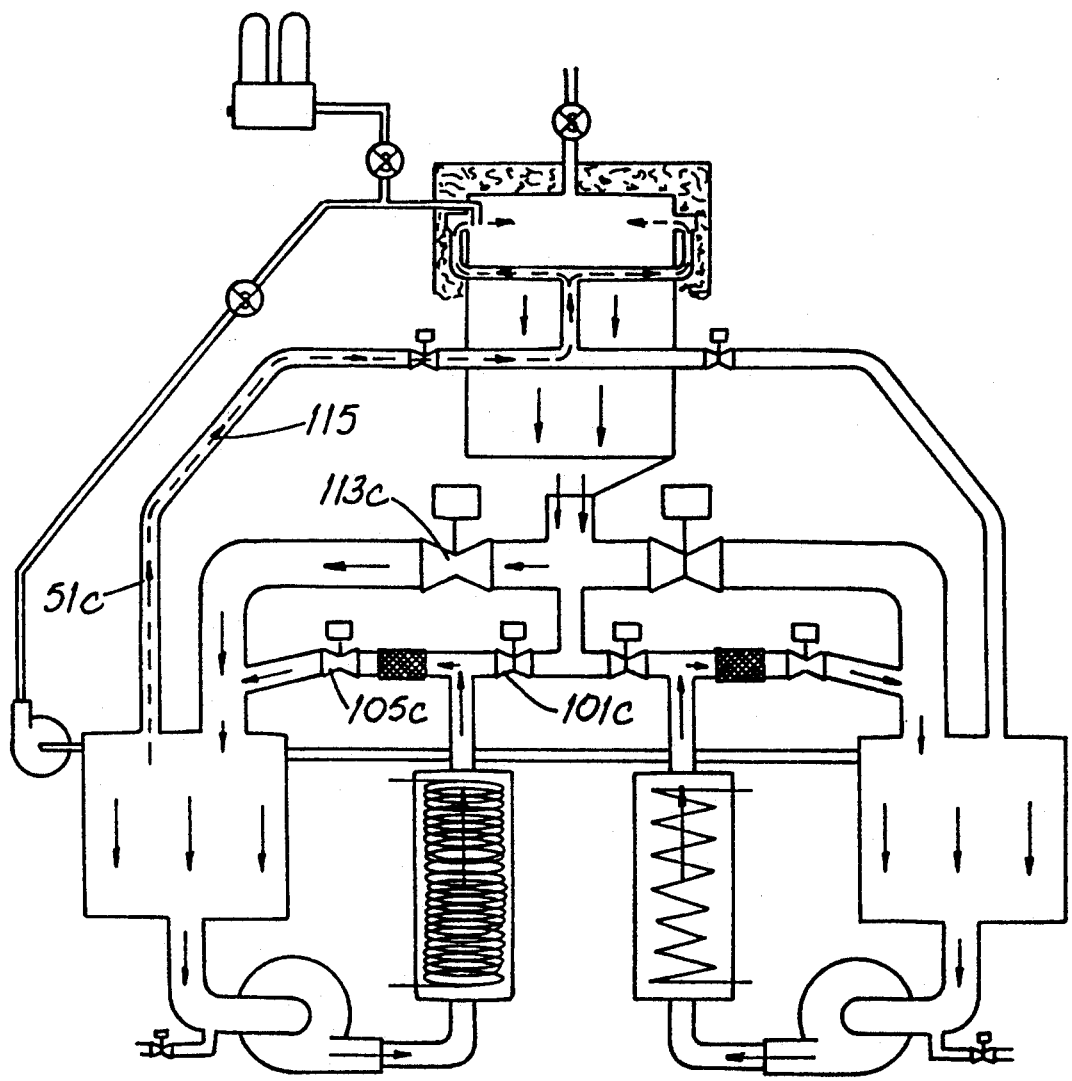
FIG. 7 is a representative diagram of the inventive system during a cold liquid drain cycle of the thermal stress screening process. Parts are in cross-section and other parts are broken away.

Referring next to FIG. 7, to transfer cold liquid 19c from the chamber 13 back into the tank 29c, the loop valve 105c and the return valve 113c are opened and the flow valve 101c is closed, thereby draining the cold liquid 19c from the chamber 13, perhaps aided by the outflow pump 49c. In so doing, air in the tank 29c is displaced along the normalizing line 51c in the direction of the arrow 115 to refill the chamber 13. During and following chamber draining, the liquid 19c is conditioned in the loop 23c (by removing heat from such liquid) so that the drained cold liquid 19c is maintained at a temperature substantially equal to the depressed temperature. During the described cold cycle portion of the process, the hot conditioning loop 23h continues to maintain the liquid 19h in the hot tank 29h at an elevated temperature, the precise value of which depends upon the requirements of the screening process.

Figure 8:
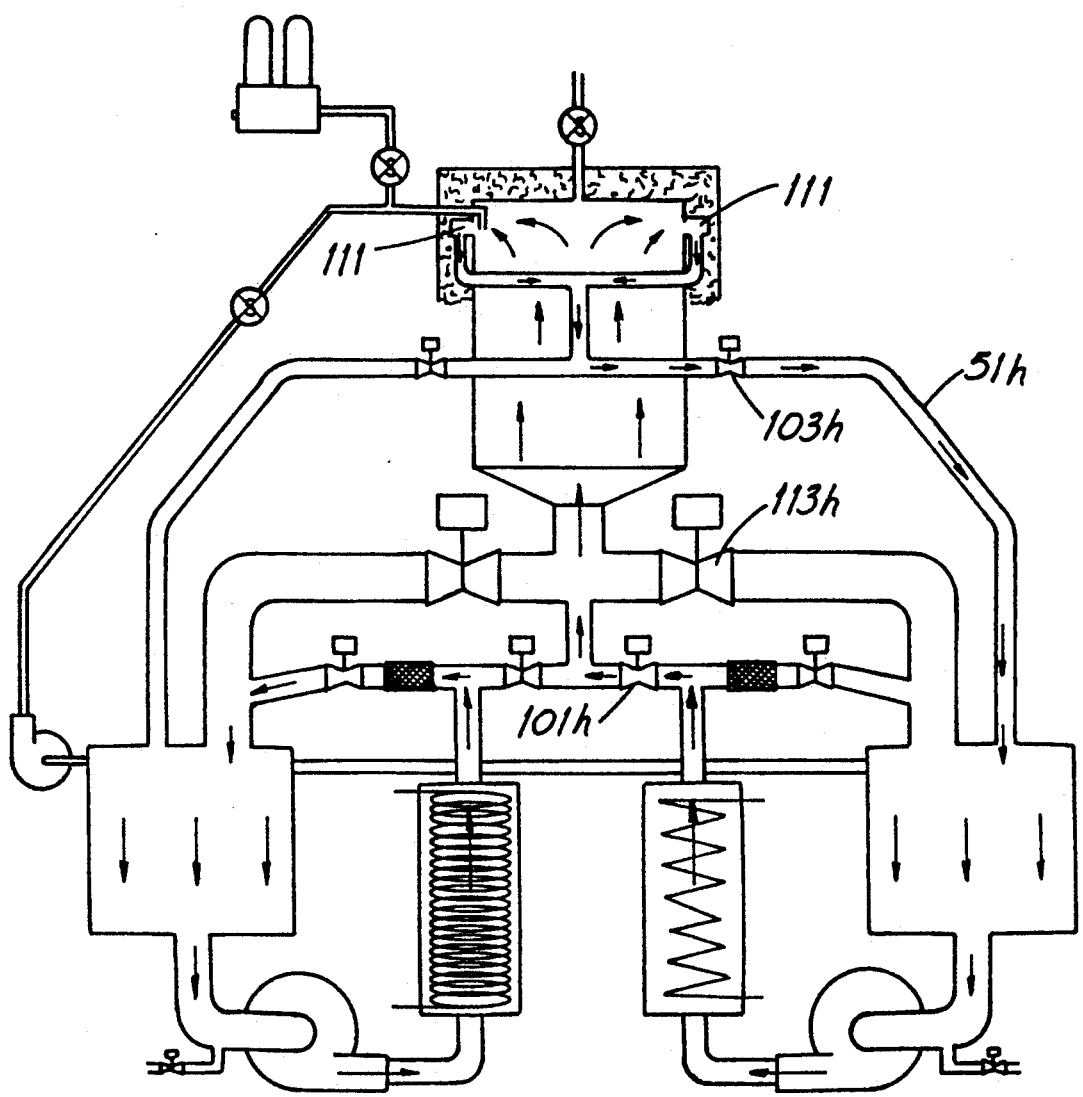
FIG. 8 is a representative diagram of the inventive system during a hot cycle portion of the thermal stress screening process. Parts are in cross-section and other parts are broken away.

Referring now to FIG. 8, a hot cycle portion of the process will now be described. Flowing hot liquid 19h into the same chamber 13 is by opening the flow valve 101h and the normalizing valve 103h. As such hot liquid 19h fills the chamber 13 to a predetermined level, displaced air flows along the line 51h to fill the void in the hot tank 29h left by the transferred hot fluid 19h. Delivery of hot liquid 19h into the chamber 13 at the elevated temperature continues even though the chamber 13 fills until liquid overflows through the ports 111 and along the normalizing line 51h. Circulation of hot liquid 19h continues in this way until the temperature of the boards 35a rises to the desired upper "set point" value.

Figure 9:
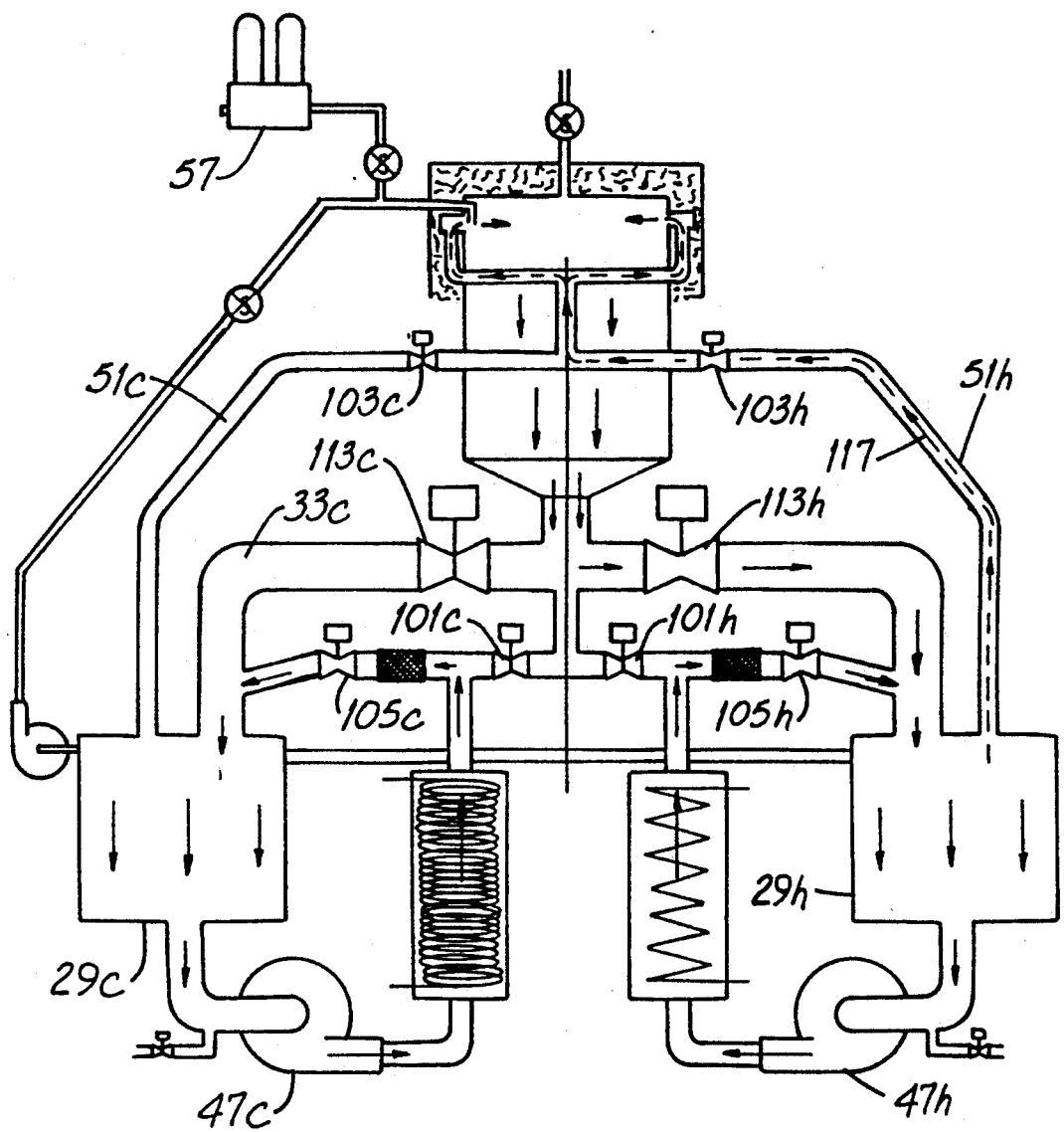
FIG. 9 is a representative diagram of the inventive system during a hot liquid drain cycle of the thermal stress screening process. Parts are in cross-section and other parts are broken away.

As shown in FIG. 9, hot liquid draining is by steps analogous to those for cold liquid draining. That is, the return valve 113h and the loop valve 105h are opened and the flow valve 101h is closed, thereby draining the hot liquid 19h from the chamber 13. In so doing, air in the tank 29h is displaced along the normalizing line 51h in the direction of the arrow 117 to refill the chamber 13. During and following chamber draining, the liquid 19h is conditioned in the loop 23h (by adding heat to such liquid 19h) so that the drained hot liquid 19h is maintained at a temperature substantially equal to the elevated temperature. During the described hot cycle portion of the process, the cold conditioning loop 23c continues to maintain the liquid 19c in the cold tank 29c at a depressed temperature, the precise value of which depends upon the requirements of the screening process.

Processing boards 35a using a cold cycle portion and a hot cycle portion changes the temperature of the boards 35a by about 145° C. or so in a period of only a few minutes, perhaps only five minutes. In contrast, systems using hot and cold air may require 30-45 minutes or so to achieve the same result.

In a highly preferred method, the last portion to be conducted in the process is a hot cycle portion. At the end of such portion, the chamber walls 69 will be hot and if the door 71 is then opened, no moisture will condense on such walls 69. However, as noted above, the chamber 13 will contain vaporized liquid 119 following the hot liquid flowing step.

Referring to FIG. 10, such step is preferably followed by the step of recovering vaporized liquid 119 from the heated chamber 13. Such recovery includes closing the return valve 113h and the normalizing valve 103h, opening the return valve 113c and the blower valve 121 and starting the blower 63. The blower 63 draws air out of the cold tank 29c and forces it into the cavity 39, thereby urging vaporized liquid 119 down the port 43 and along the return line 33 to the cold tank 29c. There, it flows through the condenser 59. In a highly preferred embodiment, the condenser 59 includes a multi-flow-path device 61 comprised of relatively thin, parallel, spaced plates 61a, a portion of which are immersed in the cold liquid 19c. Since such plates 61a will themselves be very cold, vaporized liquid 119 condenses on them and is thus returned to the tank 29c.

When vaporized liquid 119 is thus recovered, the remaining substantially vapor-free air stream is chilled to a temperature well below room ambient temperature. Recovering vaporized liquid preferably includes delivering chilled air along the cold air line 65 back to the chamber 13. Such chilled air reduces the temperature of the chamber walls 69.

However, reducing the temperature of such walls 69 too severely, i.e., below the dew point of the ambient air in the room in which the chamber 13 is located, could result in moisture condensation on the walls 69. And, as noted above, the presence of moisture in the system 10 is undesirable. Therefore, it is preferred that de-vapored chilled air is delivered to the chamber 13 until the temperature of the chamber 13 and contents are reduced to within a few degrees above the ambient temperature in that room. In that way, moisture condensation is substantially avoided even though the relative humidity in the room may be near 100%.

Referring next to FIG. 11, the preferred method may be carried out in a two-chamber system 10a as well as in a one-chamber system 10. In a two-chamber system 10a, the improved method for thermally stress screening products includes the steps of placing a first group of products 35 into a first chamber 13a, flowing cold liquid 19c into the chamber 13a and then draining the cold liquid 19c from the chamber 13a. Further steps include flowing hot liquid 19h into the same chamber 13a and in any order with respect to the placing, flowing and draining steps, the step of placing a second group of products 35 into a second chamber 13b. Therefollows the steps of flowing cold liquid 19c into the second chamber 13b, draining the cold liquid 19c from the second chamber 13b and flowing hot liquid 19h into the second chamber 13b.

Described in different terms with respect to a two-chamber arrangement 10a, the products 35 in one chamber 13a are screened by repetitively, alternately using the cold cycle and hot cycle portions of the process to screen the products 35 in that chamber 13a. While this is occurring, the second chamber 13b may be emptied of screened products 35 and re-loaded with products 35 to be screened. Then the process is carried out with respect to the products 35 in the second chamber 13b while the first chamber 13a is being emptied and re-loaded.

It is possible to carry out the process in a two-chamber arrangement 10a by using the cold cycle portion on products 35 in one chamber 13a while using the hot cycle portion on products 35 in the other chamber 13b and then alternating portion application. In such an arrangement, the piping network 11 would be more complex and substantially more heat exchange capacity would be needed.

Certain of the FIGURES (e.g., FIGS. 1 and 5) show solenoid-operated valves (e.g., valve 121) and valves (e.g., valve 101c) with other types of actuators. It is to be understood that such valves are only exemplary and that the illustrated valves may be manually actuated or may be power actuated as, e.g., by solenoid, motor or otherwise in any "mix" of actuators in the system 10 or 10a.

A preferred liquid 19 is Fluorinert TM, formula 6001, sometimes known as formula FC-48, made by Minnesota Mining and Manufacturing Co. of St. Paul, Minn. (3M). Such liquid 19 is electrically non-conductive, has a pour point of about $-62°$ C. (about $-80°$ F.), a boiling point of about 174° C. (about 315° F.), a specific gravity about 1.94 (that of water being 1.0), a viscosity of 3.1 centistokes, a specific heat of 0.24 calories/gram (°C.) and a heat of vaporization at the boiling point of 19 calories/gram.

While the principles of the invention have been described in connection with specific embodiments, such description and the embodiments are intended to be exemplary and not limiting.

We claim:

1. In a system having a chamber for stress screening products and tanks separate from the chamber for storing a hot and a cold thermal transfer liquid, respectively, the system using a single type of liquid for alternately transferring heat to and from the products, the improvement wherein the system includes:
   a closed loop liquid flow path for circulating liquid across a heat exchanger and maintaining the temperature of the liquid substantially at a predetermined value during product test, the liquid flow path including the chamber and a chamber overflow port;
   at least one conditioning loop having a closed flow path which excludes the chamber and around which liquid is circulated to maintain liquid temperature substantially at a predetermined value.

2. The system of claim 1 wherein liquid is transferred into and out of the chamber and the chamber includes at least one port substantially normalizing chamber pressure during liquid transfer.

3. The system of claim 1 wherein the chamber includes a bidirectional flow path in flow communication with the chamber and further includes a main cavity and a diffuser interposed between the flow path and the cavity and thermal transfer liquid flows through the diffuser when being introduced into the chamber.

4. The system of claim 3 wherein the product comprises printed circuit boards and the chamber includes a powered top access door and a door-supported carrier for placing a plurality of boards into the chamber.

5. The system of claim 3 wherein the chamber includes a side access door having an inner seal, an outer lip and a liquid recovery drain between the outer lip and the inner seal.

6. The system of claim 1 wherein the liquid has a top surface and the chamber contains:
   a movable carrier
   a first stationary connector;
   a second connector wired to the first connector and mounted to move with the carrier; and,
   the connectors are above the top surface of the liquid, whereby severe thermal stress of the connectors is substantially avoided.

7. The system of claim 1 wherein that tank storing cold liquid is a cold tank and the conditioning loop includes a vapor condenser within the cold tank whereby vaporized liquid is recovered in the cold tank.

8. The system of claim 7 wherein the vapor condenser includes a multi-flowpath device in the cold tank.

9. The system of claim 1 including:
   a tank for containing the liquid;
   a return line extending from the chamber to the tank; and,
   an outflow pump connected to the return line for urging liquid from the chamber toward the tank.

10. The system of claim 1 including:
   a piping network in flow communication with the tanks and the chamber; and,
   an imperforate drip receptacle below the tanks and below substantially the entirety of the network.

11. The system of claim 10 including a separate equalizing line extending between the chamber and each tank for maintaining the system at substantially ambient pressure.

12. An improved method for thermal stress screening products by using a single type of liquid for alternately transferring heat to and from the product, the method including the steps of:
   placing the product in a chamber;
   flowing cold liquid along a closed loop flow path and into the chamber;
   circulating liquid through a heat exchanger and maintaining the temperature of the liquid substantially at a predetermined value during product cold test;
   draining substantially the entirety of the cold liquid from the chamber along the closed loop flow path;
   flowing drained cold liquid through a closed conditioning loop to reduce the temperature thereof;
   flowing hot liquid into the same chamber;
   draining substantially the entirety of the hot liquid from the chamber; and,
   flowing the drained hot liquid through another closed conditioning loop to raise the temperature thereof.

13. The method of claim 12 wherein the product placing step is followed by the step of dehumidifying the chamber until the air therein is substantially free of vaporized water.

14. The method of claim 13 wherein the dehumidifying step includes purging the chamber with a substantially dry gas.

15. The method of claim 14 wherein the gas is air.

16. The method of claim 12 wherein following the hot liquid draining step, the chamber contains vaporized liquid and the hot liquid draining step is followed by the steps of:
   removing vaporized liquid from the heated chamber;
   condensing the vaporized liquid in a cold tank by using cold liquid as the thermal transfer medium; and
   storing the condensed liquid in the cold tank.

17. The method of claim 16 wherein recovering vaporized liquid includes flowing vaporized liquid through a condenser.

18. The method of claim 16 wherein recovering vaporized liquid includes delivering chilled air to the chamber.

19. The method of claim 16 wherein the chamber is in a room at an ambient temperature, the temperature of the chilled air is below room ambient and de-vapored chilled air is delivered to the chamber until the temperature of the chamber cavity is reduced to within a few degrees of the ambient temperature.

20. An improved method for thermally stress screening products including the steps of:
   providing a single thermal transfer piping network connectable to a first chamber or to a second chamber;
   placing a first group of products into the first chamber;
   flowing cold liquid from the network into the first chamber;
   circulating liquid through a heat exchanger and maintaining the temperature of the liquid substantially at a predetermined value during product cold test;
   draining the cold liquid from the first chamber back into the network at the end of a product cold test;
   flowing hot liquid from the network into the same chamber; and,
in any order with respect to the placing, flowing and draining steps, the step of:
   placing a second group of products into the second chamber;
and further including the steps of:
   flowing cold liquid from the network into the second chamber;

draining the cold liquid from the second chamber back into the network; and, flowing hot liquid from the network into the second chamber.

21. In a system having a chamber for stress screening products and tanks separate from the chamber for confining a hot and a cold thermal transfer liquid, respectively, the system using a single type of liquid for alternately transferring heat to and from the product, the improvement wherein:

the chamber has a bi-directional flow path at the bottom of the chamber through which hot and cold liquid are both introduced into the chamber and removed from the chamber;

the system includes at least one closed conditioning loop having a flow path which excludes the chamber and around which liquid is circulated to maintain liquid temperature substantially at a predetermined value.

22. The system of claim 21 wherein the closed conditioning loop is a cold loop having a pump and a heat exchanger downstream of the pump whereby heat added to the liquid by the pump is subsequently removed by the heat exchanger.

* * * * *